United States Patent [19]
Brouwer et al.

[11] Patent Number: 6,143,780
[45] Date of Patent: Nov. 7, 2000

[54] N-ARYLMETHYLTHIOANILIDE COMPOUNDS USEFUL FOR THE INHIBITION OF THE REPLICATION OF HIV

[75] Inventors: Walter Gerhard Brouwer, Guelph; Ewa Maria Osika, Kitchener, both of Canada

[73] Assignees: Uniroyal Chemical Company, Inc., Middlebury, Conn.; Uniroyal Chemical Co./CIE., Elmira, Canada

[21] Appl. No.: 09/398,649

[22] Filed: Sep. 17, 1999

[51] Int. Cl.$^7$ ............... A61K 31/505; A61K 31/381; C07D 307/68; C07D 333/38; C07D 405/12

[52] U.S. Cl. ............... 514/471; 514/256; 514/274; 514/336; 514/438; 514/444; 514/448; 544/316; 544/333; 546/280.4; 546/283.4; 546/284.4; 549/59; 549/60; 549/72; 549/473; 549/487

[58] Field of Search ............... 544/316, 333; 546/280.4, 284.4, 283.4; 549/59, 60, 72, 473, 487; 514/256, 274, 336, 444, 438, 448, 471

[56] References Cited

U.S. PATENT DOCUMENTS 5,696,151  12/1997  Brouwer et al. ............... 514/448
6,017,947   1/2000  Brouwer et al. ............... 514/438

*Primary Examiner*—Emily Bernhardt
*Assistant Examiner*—Ben Schroeder
*Attorney, Agent, or Firm*—Daniel Reitenbach

[57] ABSTRACT

Compounds of the formula

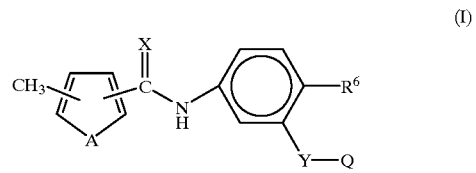

(I)

wherein

A and X are independently oxygen or sulphur;

$R^6$ is H, halogen, alkyl, alkoxy, alkylthio, cyano, or nitro;

Y is —$CH_2O$—, —$OCH_2$—, —$CH_2S$—, or —$CH_2SO_2$—;

Q is a substituted or unsubstituted phenyl or aromatic heterocyclic group:

useful for the inhibition of the replication of HIV-1, in vitro and in vivo.

28 Claims, No Drawings

N-ARYLMETHYLTHIOANILIDE COMPOUNDS USEFUL FOR THE INHIBITION OF THE REPLICATION OF HIV

FIELD OF THE INVENTION

This invention relates to N-arylmethylthioanilide compounds useful for the inhibition of the replication of HIV. This invention also relates to a method for the prevention or treatment of HIV-1 infection in a patient which comprises administering to the patient an effective amount of the N-arylmethylthioanilide compounds.

BACKGROUND OF THE INVENTION

Various compounds have been described as inhibitors of human immunodeficiency virus type 1 (HIV-1) in vitro and are targeted at the virus-encoded reverse transcriptase (RT), e.g., nevirapine, pyridinone, TIBO, BHAP, TSAO, and quinoxaline. U.S. Pat. Nos. 5,268,389 and 5,693,827 describe certain compounds useful for inhibiting the replication of HIV. The selectivity of these compounds for HIV-1 is due to a highly specific interaction with HIV-1 RT.

The rapid emergence of HIV-1 strains resistant to several HIV-1 specific RT inhibitors in cell culture and in AIDS patients has caused concern for further development of these inhibitors in the clinic. For example, HIV-1 strains containing the 100 Leu→Ile mutation in their RT are resistant to TIBO R82913 and R82150. HIV-1 strains containing the 138 Glu→Lys mutation in their RT are resistant to TSAO derivatives. The 181 Tyr→Cys mutation in the RT of HIV-1 strains renders the mutant viruses resistant to nevirapine and pyridinone. See, e.g. Balzarini et al, J. Virology 67(9): 5353–5359 (1993) ("Balzarini I") and Balzarini et al. Virology 192: 246–253 (1993) ("Balzarini II"). Attempts have been made to combine various HIV-1 RT inhibitors to eliminate virus resistance. See, e.g., Balzarini I.

U. S. Pat. No. 5,696,151 describes certain methylfuranyl- and methylthienyl-pentenylether derivatives useful against HIV-1 and HIV-1 reverse transcriptase mutants.

It is the purpose of this invention to provide new compounds which by themselves, can inhibit or suppress the emergence of wild-type HIV-1 and HIV-1 RT mutant strains. It is also the purpose of this invention to provide a method of preventing or treating HIV-1 infections by administration of such compounds.

SUMMARY OF THE INVENTION

This invention relates to a compound of the formula

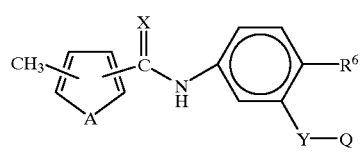

(I)

wherein
A and X are independently oxygen or sulphur;
$R^6$ is H, halogen, $C_1$–$C_4$ alkyl, $C_1$–$C_4$ alkoxy, $C_1$–$C_4$ alkylthio, cyano, or nitro;
Y is —$CH_2O$—, —$OCH_2$—, —$CH_2S$—, or —$CH_2SO_2$—;

Q is:
(A) an aromatic group of the structure

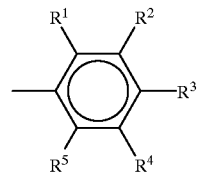

(A)

wherein $R^1$ to $R^5$ are each independently:
(i) hydrogen, halogen, $C_1$–$C_6$ alkyl, $C_1$–$C_4$ alkoxy, $C_1$–$C_4$ alkylthio, $C_1$–$C_4$ haloalkoxy, cyano, nitro, hydroxy, acetyloxy, benzoyloxy, amino, acetamido, phenyl, acetyloxymethyl, hydroxymethyl, trihalomethyl, carboxy, ($C_1$–$C_4$ alkoxy)carbonyl, formyl, ($C_1$–$C_4$ alkyl)carbonyl, benzoyl, or
(ii) a group of the formula

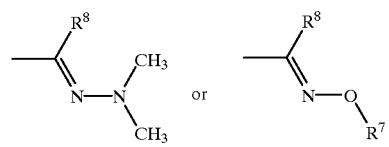

wherein $R^7$ is H, linear or branched $C_1$–$C_4$ alkyl, $C_1$–$C_4$ haloalkyl, aminocarbonylmethyl, ($C_1$–$C_6$ alkoxy)carbonylmethyl, cyanomethyl, or arylmethyl and $R^8$ is hydrogen or methyl;
or
(B) a group of the formula

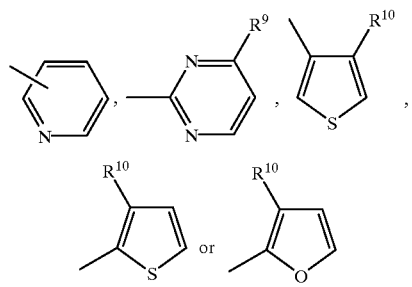

wherein
$R^9$ is hydrogen, $C_1$–$C_4$ alkyl, or $C_1$–$C_4$ haloalkyl, and
$R^{10}$ is H, halogen, $C_1$–$C_4$ alkyl or ($C_1$–$C_4$ alkoxy)-carbonyl.

The compounds of this invention are useful for the inhibition of the replication of Human Immunodeficiency Virus-1 (HIV-1), in vitro and in vivo. The compounds are useful in the therapeutic or prophylactic treatment of diseases caused by HIV-1 thereof, such as acquired immune deficiency syndrome (AIDS).

This invention additionally relates to a pharmaceutical composition comprising a therapeutically effective amount of the compound of formula I and a pharmaceutically acceptable carrier.

This invention also relates to a method of treating HIV-1 infection in an afflicted host which comprises administering to the host a therapeutically effective amount of the compound of formula I.

DESCRIPTION OF THE INVENTION

Preferred compounds of this invention are those compounds of formula I wherein:

A is oxygen or sulfur;
X is sulfur;
$R^6$ is halogen, $C_1$–$C_4$ alkyl, $C_1$–$C_4$ alkoxy, $C_1$–$C_6$ alkylthio, or cyano
Y is —$CH_2O$—, —$OCH_2$—, or —$CH_2S$—;
Q is an aromatic group of the structure

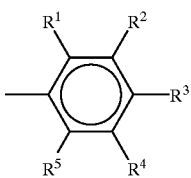

(A)

wherein $R^1$ to $R^5$ are each independently hydrogen, halogen, $C_1$–$C_6$ alkyl, $C_1$–$C_6$ alkoxy, trihalomethyl, cyano, nitro, or trihalomethoxy.

More preferred are those compounds of formula I wherein
A is oxygen or sulfur;
X is sulfur;
$R^6$ is halogen, methoxy, or cyano
Y is —$CH_2O$— or —$OCH_2$—;
Q is an aromatic group of the structure

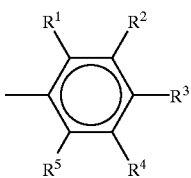

(A)

wherein $R^1$ to $R^5$ are each independently hydrogen, fluoro, chloro, methyl, methoxy, trifluoromethyl, trifluoromethoxy, cyano, or nitro, wherein one or more of $R^2$, $R^3$, $R^4$, and $R^5$ are hydrogen.

Particularly preferred is the compound of the formula

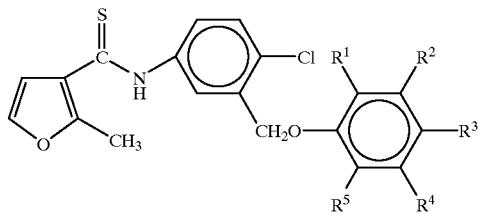

(IA)

wherein $R^1$ to $R^5$ are each independently hydrogen, fluoro, chloro, methyl, methoxy, trifluoromethyl, trifluoromethoxy, cyano, or nitro, wherein one or more of $R^2$, $R^3$, $R^4$, and $R^5$ are hydrogen.

More particularly preferred are the compounds of formula IA wherein $R^1$ is fluoro and one or more of $R^2$, $R^3$, $R^4$, and $R^5$ are hydrogen.

Method of Synthesis

The compounds of this invention can be prepared according to the following scheme (A, X, Y, Q, and $R^6$ are as defined above):

(1) Acid chloride formation

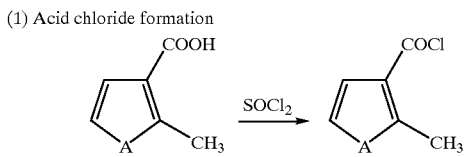

(2) Substituted protected hydroxymethyl aniline preparation

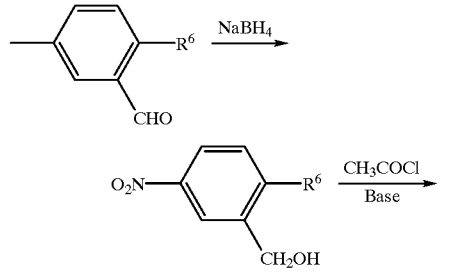

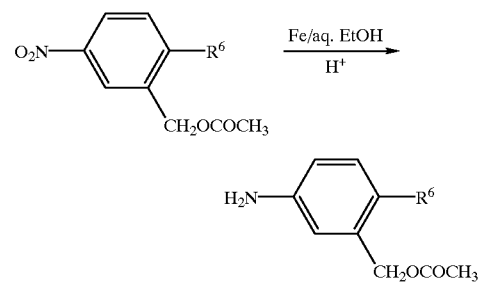

(3) Amide Formation

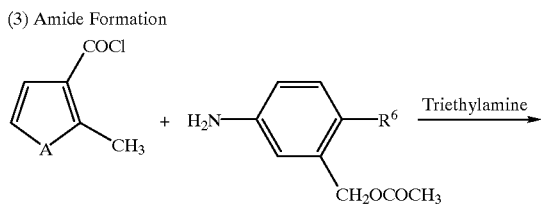

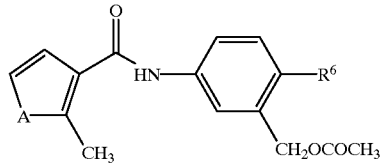

(4) Deprotection, bromination

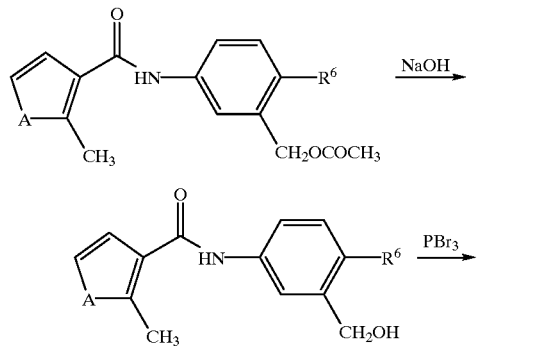

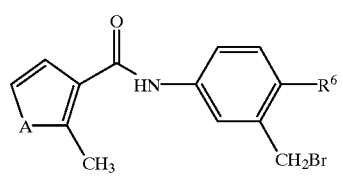

-continued (5) Arylation

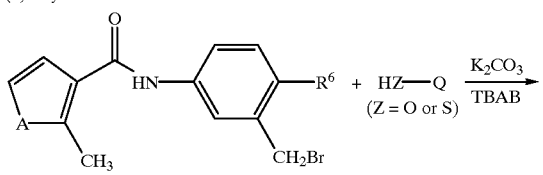

(6) Thionylation

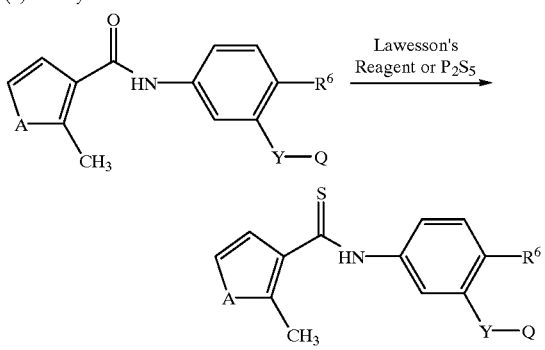

The compounds of the present invention can be administered orally, parenterally, sublingually, by inhalation spray, rectally, or topically in dosage unit formulations containing conventional non-toxic pharmaceutically acceptable carriers, adjuvants, and vehicles. Pharmaceutically acceptable carriers, adjuvants and vehicles useful in the composition of this invention can be found in standard pharmaceutical texts such as, e.g., *Remington's Pharmaceutical Sciences*, 16th Edition, Mack Publishing Company, Easton, Pa. (1980).

The therapeutically effective amount of the compounds of this invention that can be combined with the pharmaceutically acceptable carrier to produce a single dosage form will vary depending upon the age and condition of the host treated and the particular mode of administration. In general, the compounds of this invention are most desirably administered at a concentration level that will generally afford antivirally effective results without causing any harmful or deleterious side effects.

While the compounds of this invention can be administered as the sole active pharmaceutical agents, the compounds can also be used in combination with one or more other pharmaceutical agents which are not deleterious to the activity of the compounds of this invention or whose combination with the compounds will not have a deleterious effect on the host treated.

The following examples are provided to illustrate the present invention.

EXAMPLES

Materials and Methods

Example 1

Preparation of N-3-((2-chlorophenoxy)methyl)-4-chlorophenyl-2-methyl-3-furancarbothioamide (Compound No. 6)

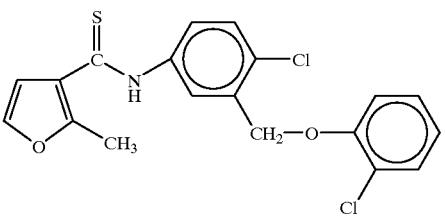

Step 1: Preparation of 2-chloro-5-nitrobenzoyl alcohol 30 g of 2-chloro-5-nitrobenzaldehyde was dissolved in 500 ml of methanol and cooled to 0° C. A solution of 10 g of sodium borohydride in 100 ml of water was then added dropwise over 90 minutes while maintaining the temperature below 10° C. The resultant reaction mixture was then stirred for one hour, then acidified with 2N HCl and left stirring overnight. The solids were then, washed with water and dried, to produce 27 g of 2-chloro-5-nitrobenzyl alcohol as a white solid.

Step 2: Preparation of 2-chloro-5-nitrobenzoyl acetate 27 g of the 2-chloro-5-nitrobenzyl alcohol prepared above in Step 1, was dissolved in 122 ml of toluene. 22 ml of triethylamine was then added. The resultant reaction mixture was cooled to 20° C. and then a solution of 10.2 ml of acetyl chloride in 10 ml of toluene, was added dropwise, keeping the temperature below 20° C. The reaction mixture was then stirred overnight. 2.1 ml of triethylamine and 1.1 ml of acetyl chloride/toluene solution were then added and the reaction mixture was stirred for one hour. 100 ml of water was then added, followed by 50 ml of ether. The resulting organic phase was separated, washed with 2N HCl, aqueous sodium bicarbonate solution and water. The washed organic phase was then dried over magnesium sulfate and the solvent was evaporated, to produce 29.6 g of 2-chloro-5-nitrobenzoyl acetate as a white solid.

Step 3: Preparation of 5-amino-2-chlorobenzoyl acetate 24 g of iron powder was added to a solution of 1.6 ml of concentrated HCl, 16.8 ml of water, and 70 ml of ethanol. 29.6 g of the 2-chloro-5-nitrobenzoyl acetate prepared above in Step 2 dissolved in 45 ml of ethanol, was then added to the mixture in three equal portions. The resultant reaction mixture was refluxed for 5 hours. An additional 2.4 g of iron and 0.1 ml of concentrated HCl was then added to the reaction mixture. The reaction mixture was then refluxed for an additional one hour, filtered through Celite and evaporated. 100 ml of water was then added to the evaporated material and the resultant mixture was extracted with 100 ml of ether. The ether solution was washed with water, dried over magnesium sulfate, and evaporated, to produce 22.9 g of 5-amino-2-chlorobenzoyl acetate as an oil.

Step 4: Preparation of N-(3-acetoxymethyl-4-chlorophenyl)-2-methyl-3-furancarboxanilide A solution of 22.8 g of the 5-amino-2-chlorobenzoyl acetate from Step 3 above and 17.2 ml of triethylamine in 118 ml ether was prepared and then added dropwise to a second solution of 16.6 g 2-methyl-3-thiophenecarboxylic acid chloride in 118 ml ether at 0° C. to 10° C. and the resultant mixture was stirred at room temperature overnight. 100 ml of water and 100 ml of ethyl acetate were then added to the mixture, the organic phase separated, washed with 2N hydrochloric acid and water, dried over magnesium sulfate, and the solvents removed in vacuo, to produce 29.87 g of N-(3-acetoxymethyl-4-chlorophenyl)-2-methyl-3-furancarboxamide as a beige solid.

Step 5: Preparation of N-(4-chloro-3-hydroxymethylphenyl)-2-methyl-3-furancarboxamide A solution of 29 g of the N-(3-acetoxymethyl-4-chlorophenyl)-2-methyl-3-furancarboxamide prepared in Step 4 above and 14.5 g potassium hydroxide in 110 ml water, was prepared. The solution was then heated at 70° C. for 16 hours and then acidified with 2N hydrochloric. The solid so produced collected, washed with water, and dried, producing 23.65 g of N-(4-chloro-3-hydroxymethylphenyl)-2-methyl-3-furancarboxamide as a white solid.

Step 6: Preparation of N-(3-bromomethyl-4-chlorophenyl)-2-methyl-3-furancarboxamide 12 g of the N-(4-chloro-3-hydroxymethylphenyl)-2-methyl-3-furancarboxamide prepared in Step 5 above, was dissolved in 180 ml ethyl acetate. 1.8 ml of phosphorus tribromide was then added. The resultant mixture was stirred for 90 minutes at room temperature. 100 ml of water was then added to the mixture. The resultant organic phase was separated, washed with water, aqueous sodium bicarbonate solution and water, and then dried over magnesium sulfate. The solvent was evaporated off to produce 12.97 g of N-(3-bromomethyl-4-chlorophenyl)-2-methyl-3-furancarboxamide as a solid.

Step 7: Preparation of N-3-((2-chlorophenoxy)methyl)-4-chlorophenyl-2-methyl-3-furancarboxamide 2 g of the N-(3-bromomethyl-4-chlorophenyl)-2-methyl-3-furancarboxamide produced in Step 6, was dissolved in 20 ml of 2-butanone to produce a solution. 0.84 g of potassium carbonate, 0.79 g of 2-chlorophenol and 0.2 g of tetrabutylammonium bromide were then added to the solution. The resultant reaction mixture was stirred at room temperature overnight, the solvents removed in vacuo, and the residue extracted with ethyl acetate, to produce a second solution. This second solution was washed with 2N aqueous sodium hydroxide and water, and then dried over magnesium sulfate. The solvent was removed to produce 2.7 g of a solid, which was purified by dissolving in ethyl acetate:hexane (20:80) and running the resultant solution through a plug of silica gel. Removal of solvent produced 2.0 g of N-3-((2-chlorophenoxy)methyl)-4-chlorophenyl-2-methyl-3-furancarboxamide as a white solid.

Step 8 Preparation of N-3-((2-chlorophenoxy)methyl)-4-chlorophenyl-2-methyl-3-furancarbothioamide 1.5 g of the N-3-((2-chlorophenoxy)methyl)-4-chlorophenyl-2-methyl-3-furancarboxamide prepared in Step 7 above, 0.8 g of Lawesson's reagent (0.8 g) and 1.6 g of sodium bicarbonate were added to 35 ml of toluene, and the resultant reaction mixture was refluxed for five hours. The reaction mixture was then passed through a plug of neutral aluminum oxide, eluted with 1:1 ether/hexane and purified by column chromatography on silica gel, to produce 0.77 g of N-3-((2-chlorophenoxy)methyl)-4-chlorophenyl-2-methyl-3-furancarbothioamide as a yellow solid, mp 116–117° C. Nuclear magnetic resonance and mass spectra were consistent with the claimed structure.

The other compounds listed in Table 1 were prepared in similar manner.

TABLE 1

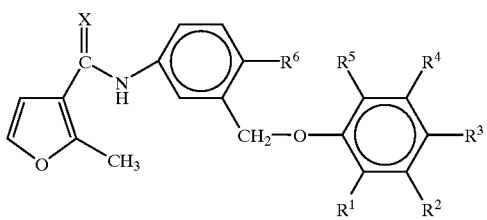

| No. | X | $R^1$ | $R^2$ | $R^3$ | $R^4$ | $R^5$ | $R^6$ |
|-----|---|-------|-------|-------|-------|-------|-------|
| 1 | O | H | H | H | H | H | Cl |
| 2 | S | H | H | H | H | H | Cl |
| 3 | O | Cl | H | H | H | H | Cl |
| 4 | O | H | Cl | H | H | H | Cl |
| 5 | S | H | $CF_3$ | H | H | H | Cl |
| 6 | S | Cl | H | H | H | H | Cl |
| 7 | S | H | Cl | H | H | H | Cl |
| 8 | S | $CH_3$ | H | H | H | H | Cl |
| 9 | S | $CH_3$ | H | H | H | H | Cl |
| 10 | O | H | H | F | H | H | Cl |
| 11 | S | H | H | F | H | H | Cl |
| 12 | O | $OCH_3$ | H | H | H | H | Cl |
| 13 | O | $NO_2$ | H | H | H | H | Cl |
| 14 | O | F | H | H | H | H | Cl |
| 15 | S | $CH_2OCOCH_3$ | H | H | H | H | Cl |
| 16 | S | F | H | H | H | F | Cl |
| 17 | O | $CH_2CH$ | H | H | H | H | Cl |
| 18 | S | F | H | H | H | H | Cl |
| 19 | S | $NO_2$ | H | H | H | H | Cl |
| 20 | O | F | H | H | H | F | Cl |
| 21 | O | $CH_2OCOCH_3$ | H | H | H | H | Cl |
| 22 | S | $OCH_3$ | H | H | H | H | Cl |
| 23 | O | $CH_2OTBDMSi^\dagger$ | H | H | H | H | Cl |
| 24 | S | $CH_2OTBDMSi^\dagger$ | H | H | H | H | Cl |
| 25 | S | $CH_2OH$ | H | H | H | H | Cl |
| 26 | O | H | $NO_2$ | H | H | H | Cl |
| 27 | S | H | $NO_2$ | H | H | H | Cl |
| 28 | S | $OCH_3$ | H | H | H | $OCH_3$ | Cl |
| 29 | O | CN | H | H | H | H | Cl |
| 30 | S | CN | H | H | H | H | Cl |
| 31 | O | F | H | H | H | $OCH_3$ | Cl |
| 32 | O | Cl | H | H | $CH_3$ | H | Cl |
| 33 | S | $OCOCH_3$ | H | H | H | H | Cl |
| 34 | S | F | H | H | H | $OCH_3$ | Cl |
| 35 | O | Br | H | H | H | H | Cl |
| 36 | S | $OCH_2CH_3$ | H | H | H | H | Cl |
| 37 | S | Cl | H | H | $CH_3$ | H | Cl |
| 38 | O | $CH_2CH_3$ | H | H | H | H | Cl |
| 39 | O | F | F | H | H | F | Cl |
| 40 | S | Br | H | H | H | H | Cl |
| 41 | O | $CF_3$ | H | H | H | H | Cl |
| 42 | O | Cl | H | F | H | H | Cl |
| 43 | S | $CH_2CH_2CH_3$ | H | H | H | H | Cl |
| 44 | S | $CH_2CH_3$ | H | H | H | H | Cl |
| 45 | S | F | F | H | H | F | Cl |

TABLE 1-continued

| No. | X | R¹ | R² | R³ | R⁴ | R⁵ | R⁶ |
|---|---|---|---|---|---|---|---|
| 46 | S | CF₃ | H | H | H | H | Cl |
| 47 | S | Cl | H | F | H | H | Cl |
| 48 | S | C₆H₅ | H | H | H | H | Cl |
| 49 | S | t-butyl | H | H | H | H | Cl |
| 50 | S | CH=NOCH₂CH₃ | H | H | H | H | Cl |
| 51 | S | COOCH₃ | H | H | H | H | Cl |
| 52 | O | NH₂ | H | H | H | H | Cl |
| 53 | S | OH | H | H | H | H | Cl |
| 54 | S | COCH₃ | H | H | H | H | Cl |
| 55 | S | OCH₂CH₂CH₃ | H | H | H | H | Cl |
| 56 | O | C(CH₃)=NN(CH₃)₂ | H | H | H | H | Cl |
| 57 | S | CH=NN(CH₃)₂ | H | H | H | H | Cl |
| 58 | O | F | F | H | F | F | Cl |
| 59 | S | F | F | F | F | F | Cl |
| 60 | S | F | F | H | F | F | Cl |
| 61 | O | F | F | H | H | F | Br |
| 62 | O | CF₃ | H | H | H | H | Br |
| 63 | O | F | H | H | H | OCH₃ | Br |
| 64 | S | F | F | H | H | F | Br |
| 65 | S | CF₃ | H | H | H | H | Br |
| 66 | S | F | H | H | H | OCH₃ | Br |

[554] TBDMSi = tert-butyldimethylsilyl

TABLE 1B

| No. | X | Y | Q |
|---|---|---|---|
| 67 | O | CH₂S | 2-chlorophenyl |
| 68 | S | CH₂S | 2-chlorophenyl |
| 69 | O | OCH₂ | 2-fluorophenyl |
| 70 | S | OCH₂ | 2-fluorophenyl |
| 71 | S | CH₂S | 2-fluorophenyl |
| 72 | O | CH₂S | 2-fluorophenyl |
| 73 | O | CH₂O | 2-(methoxycarbonyl)-3-thienyl |
| 74 | S | CH₂O | 2-(methoxycarbonyl)-3-thienyl |
| 75 | O | OCH₂ | 3-bromo-2-thienyl |
| 76 | S | OCH₂ | 3-bromo-2-thienyl |
| 77 | S | CH₂SO₂ | 2-chlorophenyl |
| 78 | S | CH₂S | 2-pyrimidinyl |
| 79 | O | CH₂S | 2-pyridinyl |
| 80 | S | CH₂S | 2-pyridinyl |
| 81 | O | CH₂O | 3-pyridinyl |
| 82 | O | OCH₂ | 2-methyl-3-furanyl |
| 83 | S | CH₂S | 4-pyridinyl |
| 84 | S | OCH₂ | 2-methyl-3-furanyl |
| 85 | S | CH₂O | 3-pyridinyl |

Cells and Viruses

CEM cells were obtained from the American Tissue Cell Culture Collection (Rockville, Md.). HIV-1 (III$_B$) was originally obtained from the culture supernatant of persistently HIV-1-infected H9 cells and was provided by R. C. Gallo and M. Popovic (National Cancer Institute, National Institutes of Health, Bethesda, Md.).

The selection and characterization of the HIV-1 RT mutant strains were done as follows: HIV-1/100-Ile ("100-Ile") was selected for resistance against TIBO R82150 as described in Balzarini et al, Virology 192: 246–253 (1993); HIV-1/103-Asn ("103-Asn") was selected for resistance against TIBO R82913 as described in Balzarini et al, Virology 192: 246–253 (1993); HIV-1/106-Ala ("106-Ala") was selected for resistance against nevirapine as described in Balzarini et al, J. Virol. 67: 5353–5359 (1993); HIV-1/Lys-138 ("Lys-138") was selected for resistance against TSAO-m³T as described in Balzarini et al, Virology 192: 246–253 (1993) and Balzarini et al, Proc. Nat. Acad. Sci. USA 90: 6952–6956 (1993); HIV-1/181-Cys ("181-Cys") was selected for resistance against pyridinone L-697,661 as described in Balzarini et al, Virology 192: 246–253 (1993); and HIV-1/188-His ("188-His") was selected for resistance against HEPT as described in Balzarini et al, Mol. Pharmocol. 44: 694–701 (1993). 188-His was then further converted to HIV-1/188-Leu ("188-Leu") upon further passage in cell culture in the absence of the HEPT. HIV-1/101-Glu ("101-Glu") and HIV-1/190-Glu ("190-Glu") were selected for resistance against the thiocarboxanilide derivative designated as UC38 as described in Balzarini et al, Antiviral Research 27: 219–236 (1995). HIV-1/184-Ile ("184-Ile") was selected for resistance against the combination of 3TC and TSAO-m³T as described in Balzarini et al, Molecular Pharm. 49: 882–890 (1996). HIV-1/184-Val ("184-Val") was selected for resistance against 3TC as described in Balzarini et al, Molecular Pharm. 49: 882–890 (1996).

Antiviral Activity of the Test Compounds in Cell Cultures

CEM cells were suspended at ≈300,000 cells per ml of culture medium and infected with approximately 100 CCID$_{50}$ (CCID$_{50}$ being the 50% cell culture infective dose) of HIV-1(III$_B$) (designated as "WT" in Table 3) or one of the HIV-1 RT mutant strains described above. Then 100 μl of the infected cell suspensions was added to 200 μl microtiter plate wells containing 100 μl of appropriate serial (5-fold) dilutions of the test compounds. The inhibitiory effect of the test compounds on HIV-1 induced syncytium formation in CEM cells was examined microscopically on day 4 post infection. The 50% effective concentration (EC$_{50}$) was defined as the test compound concentration that inhibits syncytium formation in the HIV-1-infected cell cultures by 50%.

TABLE 2

Activity Against HIV-1 (III$_B$)

| Compound No. | EC$_{50}$ (mmol/ml) |
|---|---|
| 1 | 2.38 × 10⁻⁶, 1.55 × 10⁻⁶, 3.20 × 10⁻⁶, 4.81 × 10⁻⁶ |
| 2 | 2.28 × 10⁻⁷, 1.61 × 10⁻⁷, 9.86 × 10⁻⁸, 6.76 × 10⁻⁸ |
| 5 | 3.83 × 10⁻⁸, 3.88 × 10⁻⁶, 4.11 × 10⁻⁶, 3.84 × 10⁻⁶ |
| 6 | 5.86 × 10⁻⁸, 1.04 × 10⁻⁷ |
| 7 | 6.82 × 10⁻⁸, 5.25 × 10⁻⁸, 4.32 × 10⁻⁷ |
| 8 | 1.07 × 10⁻⁷ |
| 9 | 1.35 × 10⁻⁵, 3.50 × 10⁻⁵ |
| 10 | 4.15 × 10⁻⁶, 4.26 × 10⁻⁶, 3.79 × 10⁻⁶ |
| 11 | 8.51 × 10⁻⁸, 1.61 × 10⁻⁷, 3.65 × 10⁻⁷, 2.76 × 10⁻⁷ |
| 12 | 4.88 × 10⁻⁷, 3.79 × 10⁻⁷, 4.42 × 10⁻⁷, 8.99 × 10⁻⁷ |

TABLE 2-continued

Activity Against HIV-1 (III$_B$)

| Compound No. | EC$_{50}$ (mmol/ml) |
|---|---|
| 13 | $3.01 \times 10^{-7}$, $2.08 \times 10^{-7}$, $1.51 \times 10^{-7}$, $3.58 \times 10^{-7}$ |
| 14 | $7.71 \times 10^{-7}$, $3.95 \times 10^{-7}$, $6.64 \times 10^{-7}$, $2.55 \times 10^{-7}$ |
| 16 | $2.86 \times 10^{-8}$, $3.92 \times 10^{-8}$ |
| 17 | $1.65 \times 10^{-5}$, $4.81 \times 10^{-6}$ |
| 18 | $1.17 \times 10^{-7}$, $1.11 \times 10^{-7}$ |
| 19 | $2.71 \times 10^{-8}$, $3.93 \times 10^{-8}$ |
| 20 | $4.96 \times 10^{-7}$, $7.99 \times 10^{-7}$ |
| 22 | $1.60 \times 10^{-7}$, $2.09 \times 10^{-7}$ |
| 25 | $3.14 \times 10^{-6}$, $1.09 \times 10^{-6}$, $2.72 \times 10^{-6}$, $1.49 \times 10^{-6}$, $1.15 \times 10^{-6}$, $1.00 \times 10^{-6}$ |
| 26 | $4.61 \times 10^{-6}$, $4.14 \times 10^{-6}$, $4.94 \times 10^{-6}$, $3.66 \times 10^{-6}$ |
| 27 | $1.21 \times 10^{-7}$, $3.40 \times 10^{-7}$, $5.95 \times 10^{-7}$ |
| 28 | $6.71 \times 10^{-6}$, $7.56 \times 10^{-6}$, $9.05 \times 10^{-8}$, $1.96 \times 10^{-5}$, $1.01 \times 10^{-5}$, $1.10 \times 10^{-5}$ |
| 29 | $3.39 \times 10^{-6}$, $3.48 \times 10^{-6}$, $3.33 \times 10^{-6}$, $3.40 \times 10^{-6}$, $3.10 \times 10^{-6}$, $3.76 \times 10^{-6}$ |
| 30 | $6.35 \times 10^{-8}$, $6.87 \times 10^{-8}$, $9.79 \times 10^{-8}$, $1.03 \times 10^{-7}$ |
| 31 | $7.78 \times 10^{-8}$, $1.24 \times 10^{-7}$, $1.97 \times 10^{-7}$, $2.13 \times 10^{-7}$ |
| 32 | $4.61 \times 10^{-6}$, $2.74 \times 10^{-5}$, $9.85 \times 10^{-6}$, $1.12 \times 10^{-5}$, $2.57 \times 10^{-6}$ |
| 33 | $1.39 \times 10^{-6}$, $2.83 \times 10^{-6}$, $4.16 \times 10^{-6}$, $2.67 \times 10^{-6}$ |
| 34 | $5.65 \times 10^{-9}$, $1.74 \times 10^{-8}$ |
| 35 | $2.29 \times 10^{-6}$, $3.14 \times 10^{-6}$, $1.99 \times 10^{-6}$, $1.23 \times 10^{-6}$ |
| 36 | $3.77 \times 10^{-7}$, $1.24 \times 10^{-7}$, $1.21 \times 10^{-6}$, $7.88 \times 10^{-7}$ |
| 37 | $1.92 \times 10^{-8}$, $7.66 \times 10^{-8}$ |
| 38 | $2.88 \times 10^{-6}$, $1.45 \times 10^{-6}$, $4.70 \times 10^{-6}$ |
| 39 | $1.02 \times 10^{-7}$, $5.07 \times 10^{-8}$, $1.02 \times 10^{-7}$, $1.13 \times 10^{-7}$ |
| 40 | $3.53 \times 10^{-8}$, $4.60 \times 10^{-8}$, $7.11 \times 10^{-8}$, $1.68 \times 10^{-8}$ |
| 41 | $7.61 \times 10^{-7}$, $1.11 \times 10^{-6}$, $1.56 \times 10^{-6}$ |
| 42 | $4.66 \times 10^{-6}$, $1.82 \times 10^{-5}$ |
| 43 | $4.25 \times 10^{-8}$, $1.18 \times 10^{-7}$ |
| 44 | $3.07 \times 10^{-8}$, $1.80 \times 10^{-8}$, $6.23 \times 10^{-8}$, $9.54 \times 10^{-8}$ |
| 45 | $6.35 \times 10^{-8}$, $6.50 \times 10^{-10}$, $1.46 \times 10^{-9}$, $7.29 \times 10^{-9}$, $2.69 \times 10^{-9}$ |
| 46 | $3.93 \times 10^{-8}$, $5.48 \times 10^{-8}$, $2.11 \times 10^{-8}$, $9.14 \times 10^{-9}$ |
| 47 | $1.03 \times 10^{-6}$, $5.16 \times 10^{-7}$ |
| 48 | $3.11 \times 10^{-6}$, $2.75 \times 10^{-6}$, $6.11 \times 10^{-6}$, $5.41 \times 10^{-6}$ |
| 49 | $3.84 \times 10^{-7}$, $5.99 \times 10^{-7}$, $4.01 \times 10^{-7}$, $1.13 \times 10^{-6}$ |
| 50 | $1.43 \times 10^{-6}$, $1.43 \times 10^{-7}$, $9.06 \times 10^{-7}$, $1.07 \times 10^{-6}$ |
| 51 | $1 \times 10^{-6}$, $2.26 \times 10^{-7}$, $9.15 \times 10^{-7}$, $5.68 \times 10^{-7}$ |
| 52 | $1.37 \times 10^{-5}$, $1.62 \times 10^{-5}$, $3.28 \times 10^{-5}$ |
| 53 | $4.34 \times 10^{-6}$, $3.93 \times 10^{-8}$, $2.79 \times 10^{-6}$, $4.58 \times 10^{-6}$ |
| 54 | $6.67 \times 10^{-6}$, $1.53 \times 10^{-5}$, $5.64 \times 10^{-6}$ |
| 55 | $1.0 \times 10^{-5}$, $9.0 \times 10^{-6}$, $3.73 \times 10^{-6}$, $4.26 \times 10^{-6}$ |
| 56 | $2.23 \times 10^{-6}$, $2.91 \times 10^{-6}$, $3.54 \times 10^{-6}$, $3.58 \times 10^{-6}$ |
| 57 | $2.14 \times 10^{-7}$, $7.66 \times 10^{-8}$, $1.21 \times 10^{-7}$, $7.92 \times 10^{-8}$ |
| 58 | $4.75 \times 10^{-7}$, $2.81 \times 10^{-7}$ |
| 59 | $1.99 \times 10^{-7}$, $1.17 \times 10^{-7}$ |
| 60 | $1.06 \times 10^{-8}$, $4.62 \times 10^{-9}$ |
| 61 | $2.05 \times 10^{-9}$ |
| 62 | $1.95 \times 10^{-7}$, $8.17 \times 10^{-7}$, $5.09 \times 10^{-7}$, $5.52 \times 10^{-7}$, $7.93 \times 10^{-7}$, $5.54 \times 10^{-7}$ |
| 63 | $7.45 \times 10^{-9}$, $7.55 \times 10^{-9}$ |
| 64 | $6.21 \times 10^{-11}$, $5.87 \times 10^{-9}$ |
| 65 | $2.90 \times 10^{-10}$, $2.81 \times 10^{-10}$ |
| 69 | $3.59 \times 10^{-7}$, $3.17 \times 10^{-7}$, $1.26 \times 10^{-7}$, $2.44 \times 10^{-7}$ |
| 70 | $1.22 \times 10^{-8}$, $9.67 \times 10^{-9}$ |
| 71 | $3.42 \times 10^{-7}$, $1.28 \times 10^{-7}$, $1.60 \times 10^{-7}$, $3.96 \times 10^{-7}$ |
| 72 | $1.49 \times 10^{-5}$, $1.21 \times 10^{-5}$, $5.80 \times 10^{-6}$ |
| 73 | $1.31 \times 10^{-4}$, $2.12 \times 10^{-5}$ |
| 74 | $2.70 \times 10^{-7}$, $1.31 \times 10^{-7}$, $9.28 \times 10^{-7}$, $1.47 \times 10^{-7}$ |
| 75 | $5.88 \times 10^{-7}$, $1.50 \times 10^{-6}$, $1.09 \times 10^{-6}$, $2.60 \times 10^{-6}$ |
| 76 | $8.61 \times 10^{-8}$, $9.52 \times 10^{-8}$ |
| 77 | $2.51 \times 10^{-7}$, $2.99 \times 10^{-7}$, $4.05 \times 10^{-7}$, $1.11 \times 10^{-6}$ |
| 78 | $3.02 \times 10^{-7}$, $6.96 \times 10^{-7}$, $7.12 \times 10^{-7}$, $3.75 \times 10^{-7}$ |
| 79 | $2.83 \times 10^{-6}$, $2.99 \times 10^{-6}$, $4.04 \times 10^{-6}$, $3.30 \times 10^{-6}$, $1.65 \times 10^{-6}$, $6.14 \times 10^{-7}$ |
| 80 | $2.18 \times 10^{-7}$, $1.50 \times 10^{-7}$ |
| 81 | $5.50 \times 10^{-6}$, $3.69 \times 10^{-6}$, $1.49 \times 10^{-5}$ |
| 82 | $1.46 \times 10^{-6}$, $3.15 \times 10^{-6}$, $1.25 \times 10^{-6}$, $2.43 \times 10^{-6}$ |
| 83 | $1.65 \times 10^{-5}$, $1.33 \times 10^{-5}$, $1.05 \times 10^{-5}$, $1.21 \times 10^{-5}$ |
| 84 | $6.61 \times 10^{-8}$, $2.55 \times 10^{-7}$, $1.26 \times 10^{-7}$ |
| 85 | $1.51 \times 10^{-7}$, $2.11 \times 10^{-7}$ |

TABLE 3

Activity Against HIV-1(III$_B$) and HIV-1 RT Mutants

EC$_{50}$ ($\mu$g/ml)

| No. | WT | 100-Ile | 101-Glu | 103-Ala | 106-Ala | 138-Lys | 181-Cys | 184-Ile | 184-Val | 188-His | 188-Leu | 190-Glu |
|---|---|---|---|---|---|---|---|---|---|---|---|---|
| 5 | 0.5 | >2 | >2 | >2 | | 1.73 | 0.33 | >2 | 0.93 | >2 | | >2 |
| 6 | 0.0067 | 0.23 | 0.11 | 1.2 | | 0.025 | 0.09 | 0.047 | 0.018 | 0.053 | | >2 |
| 7 | 0.09 | 0.65 | 2 | ≧2 | | 0.33 | 0.44 | 0.4 | 0.1 | 0.95 | | ≧10 |
| 8 | 0.022 | 0.33 | 1.5 | 2 | 1 | 0.19 | 0.95 | 0.065 | 0.02 | 0.5 | 0.7 | ≧2 |
| 11 | 0.065 | 0.95 | ≧2 | >2 | 1.1 | 0.7 | 0.14 | 0.16 | 0.045 | >2 | ≧2 | ≧2 |
| 15 | 0.49 | >2 | >2 | >2 | >2 | >2 | >2 | 1.2 | 0.5 | >2 | >2 | ≧2 |
| 16 | 0.0031 | 0.08 | 0.069 | 0.6 | 0.03 | 0.018 | 0.03 | 0.011 | 0.0036 | 0.52 | 0.95 | >2 |
| 18 | 0.0053 | 0.077 | 0.24 | >2 | 1.1 | 0.53 | 0.1 | 0.032 | 0.008 | 1.73 | >2 | >2 |
| 19 | 0.0023 | 0.08 | 0.17 | 0.52 | 0.13 | 0.0075 | 0.13 | 0.0045 | 0.0041 | 0.12 | 1.35 | >2 |
| 22 | 0.011 | 0.4 | 0.75 | 2.73 | 1 | 0.075 | 0.41 | 0.025 | 0.018 | 0.85 | >2 | >2 |
| 25 | 0.55 | >2 | >2 | >2 | >2 | >2 | >2 | 1 | 0.25 | >2 | >2 | >2 |
| 27 | 0.03 | 0.7 | 0.55 | >2 | 1.57 | 0.23 | 0.5 | 0.11 | 0.4 | >2 | >2 | >2 |
| 30 | 0.006 | 0.33 | 0.63 | >2 | 0.7 | 0.042 | 0.65 | 0.03 | 0.021 | 0.35 | 0.85 | >2 |
| 34 | 0.0022 | 0.16 | 0.12 | 0.85 | 0.1 | 0.02 | 0.1 | 0.0087 | 0.005 | 0.5 | 0.53 | >2 |
| 37 | 0.025 | 2.33 | 1.4 | >2 | >2 | 0.33 | >2 | 0.14 | 0.09 | 0.33 | 0.62 | >2 |
| 40 | 0.02 | 1.73 | 0.4 | >2 | 0.85 | 0.09 | 0.75 | 0.04 | 0.018 | 0.4 | 0.7 | >2 |
| 43 | 0.03 | 1.14 | 1.35 | >2 | >2 | 0.31 | >0.4 | 0.13 | 0.04 | 0.65 | >2 | >2 |

TABLE 3-continued

Activity Against HIV-1(III$_B$) and HIV-1 RT Mutants

| | | | | | | EC$_{50}$ ($\mu$g/ml) | | | | | |
|---|---|---|---|---|---|---|---|---|---|---|---|
| No. | WT | 100-Ile | 101-Glu | 103-Ala | 106-Ala | 138-Lys | 181-Cys | 184-Ile | 184-Val | 188-His | 188-Leu | 190-Glu |
| 44 | 0.0065 | 0.41 | 0.65 | >2 | 1.1 | 0.16 | >2 | 0.04 | 0.018 | 0.25 | 0.35 | >2 |
| 45 | 0.0017 | 0.11 | 0.04 | 0.4 | 0.025 | 0.012 | 0.065 | 0.005 | 0.0027 | 0.85 | 1.5 | >2 |
| 46 | 0.0041 | 0.11 | 0.18 | 0.55 | 0.47 | 0.03 | 0.5 | 0.018 | 0.0093 | 0.16 | 0.19 | >2 |
| 47 | 0.018 | 0.65 | 1.47 | >2 | >2 | 0.64 | 1 | 0.12 | 0.05 | 2 | >2 | >2 |

What is claimed is:

1. A compound of the formula

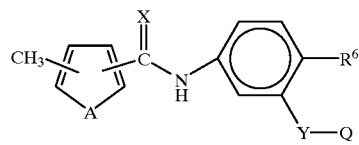

(I)

wherein

A and X are independently oxygen or sulfur;

R$^6$ is H, halogen, C$_1$–C$_4$ alkyl, C$_1$–C$_4$ alkoxy, C$_1$–C$_4$ alkylthio, cyano, or nitro;

Y is —CH$_2$O—, —OCH$_2$—, —CH$_2$S—, or —CH$_2$SO$_2$—;

Q is:

(A) a group of the structure

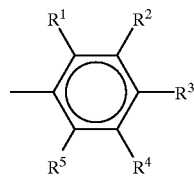

(A)

wherein R$^1$ to R$^5$ are each independently:

(i) hydrogen halogen, C$_1$–C$_6$ alkyl, C$_1$–C$_4$ alkoxy, C$_1$–C$_4$ alkylthio, C$_1$–C$_4$ haloalkoxy, cyano, nitro, hydroxy, acetyloxy, benzoyloxy, amino, acetamido, phenyl, acetyloxymethyl, hydroxymethyl, trihalomethyl, carboxy, (C$_1$–C$_4$ alkoxy)carbonyl, formyl, (C$_1$–C$_4$ alkyl)carbonyl, benzoyl, or (ii) a group of the formula

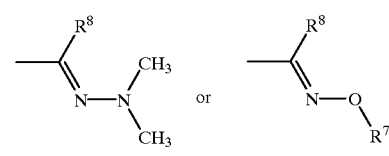

wherein R$^7$ is H, linear or branched C$_1$–C$_4$ alkyl, C$_1$–C$_4$ haloalkyl, aminocarbonylmethyl, (C$_1$–C$_6$ alkoxy)carbonylmethyl, or cyanomethyl, and R$^8$ is hydrogen or methyl;

or (B) a group of the formula

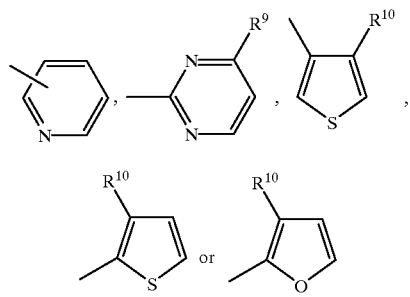

wherein

R$^9$ is hydrogen, C$_1$–C$_4$ alkyl, or C$_1$–C$_4$ haloalkyl, and

R$^{10}$ is H, halogen, C$_1$–C$_4$ alkyl or (C$_1$–C$_4$ alkoxy)-carbonyl.

2. A compound as recited in claim 1 wherein:

A is oxygen or sulfur;

X is sulfur;

R$^6$ is halogen, C$_1$–C$_4$ alkyl, C$_1$–C$_4$ alkoxy, C$_1$–C$_6$ alkylthio, or cyano Y is —CH$_2$O—, —OCH$_2$—, or —CH$_2$S—;

Q is a group of the structure

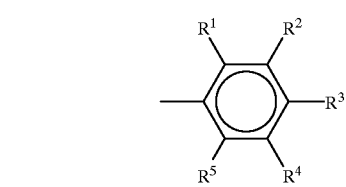

(A)

wherein R$^1$ to R$^5$ are each independently hydrogen, halogen, C$_1$–C$_6$ alkyl, C$_1$–C$_6$ alkoxy, trihalomethyl, cyano, nitro, or trihalomethoxy.

3. A compound as recited in claim 2 wherein

R$^6$ is halogen, methoxy, or cyano

Y is —CH$_2$O— or —OCH$_2$—;

Q is an aromatic group of the structure

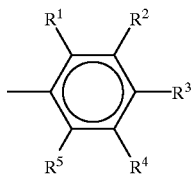
(A)

wherein $R^1$ to $R^5$ are each independently hydrogen, fluoro, chloro, methyl, methoxy, trifluoromethyl, trifluoromethoxy, cyano, or nitro, wherein one or more of $R^2$, $R^3$, $R^4$, and $R^5$ are hydrogen.

4. A compound of the formula

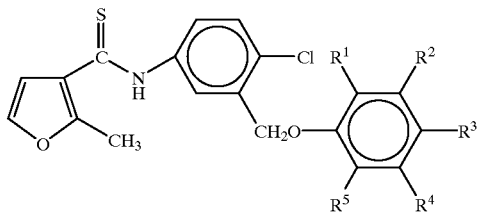

wherein $R^1$ to $R^5$ are each independently hydrogen, fluoro, chloro, methyl, methoxy, trifluoromethyl, trifluoromethoxy, cyano, or nitro, wherein one or more of $R^2$, $R^3$, $R^4$, and $R^5$ are hydrogen.

5. A compound as recited in claim 4 wherein $R^1$ and $R^5$ are fluorine, and $R^2$, $R^3$, and $R^4$ are hydrogen.

6. A compound as recited in claim 4 wherein $R^1$ is nitro, and $R^2$, $R^3$, $R^4$, and $R^5$ are hydrogen.

7. A compound as recited in claim 4 wherein $R^1$ is fluoro, $R^5$ is methoxy, and $R^2$, $R^3$, and $R^4$ are hydrogen.

8. A compound as recited in claim 4 wherein $R^1$ is bromo, and $R^2$, $R^3$, $R^4$ and $R^5$ are hydrogen.

9. A compound as recited in claim 4 wherein $R^1$, $R^2$ and $R^5$ are fluoro, and $R^3$ and $R^4$ are hydrogen.

10. A compound as recited in claim 4 wherein $R^1$ is trifluoromethyl, and $R^2$, $R^3$, $R^4$ and $R^5$ are hydrogen.

11. A compound as recited in claim 4 wherein $R^1$, $R^2$, $R^3$ and $R^5$ are fluoro, and $R^4$ is hydrogen.

12. A compound as recited in claim 4 wherein $R^1$ is fluoro, and $R^2$, $R^3$, $R^4$, and $R^5$ are hydrogen.

13. A compound of the formula

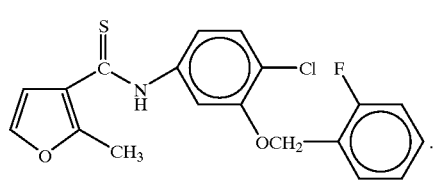

14. A pharmaceutical composition useful for treating HIV-1 infection in an infected host, which composition comprises a therapeutically effective amount of the compound as recited in claim 1 and a pharmaceutically acceptable carrier.

15. A pharmaceutical composition useful for treating HIV-1 infection in an infected host, which composition comprises a therapeutically effective amount of the compound as recited in claim 2 and a pharmaceutically acceptable carrier.

16. A pharmaceutical composition useful for treating HIV-1 infection in an infected host, which composition comprises a therapeutically effective amount of the compound as recited in claim 3 and a pharmaceutically acceptable carrier.

17. A pharmaceutical composition useful for treating HIV-1 infection in an infected host, which composition comprises a therapeutically effective amount of the compound as recited in claim 4 and a pharmaceutically acceptable carrier.

18. A pharmaceutical composition useful for treating HIV-1 infection in an infected host, which composition comprises a therapeutically effective amount of the compound as recited in claim 13 and a pharmaceutically acceptable carrier.

19. A method of treating HIV-1 infection in an afflicted host which comprises administering to the host a therapeutically effective amount of the compound as recited in claim 1.

20. A method of treating HIV-1 infection in an afflicted host which comprises administering to the host a therapeutically effective amount of the compound as recited in claim 2.

21. A method of treating HIV-1 infection in an afflicted host which comprises administering to the host a therapeutically effective amount of the compound as recited in claim 3.

22. A method of treating HIV-1 infection in an afflicted host which comprises administering to the host a therapeutically effective amount of the compound as recited in claim 4.

23. A method of treating HIV-1 infection in an afflicted host which comprises administering to the host a therapeutically effective amount of the compound as recited in claim 13.

24. A method of inhibiting the replication of HIV-1 which comprises contacting the HIV-1 with an effective amount of a compound as recited in claim 1.

25. A method of inhibiting the replication of HIV-1 which comprises contacting the HIV-1 with an effective amount of a compound as recited in claim 2.

26. A method of inhibiting the replication of HIV-1 which comprises contacting the HIV-1 with an effective amount of a compound as recited in claim 3.

27. A method of inhibiting the replication of HIV-1 which comprises contacting the HIV-1 with an effective amount of a compound as recited in claim 4.

28. A method of inhibiting the replication of HIV-1 which comprises contacting the HIV-1 with an effective amount of a compound as recited in claim 13.

* * * * *